United States Patent [19]

Webb, Jr. et al.

[11] Patent Number: 4,921,493
[45] Date of Patent: May 1, 1990

[54] RASP TOOL

[75] Inventors: John D. Webb, Jr., Etna Green; James J. Morr, Leesburg, both of Ind.

[73] Assignee: Zimmer, Inc., Warsaw, Ind.

[21] Appl. No.: 895,563

[22] Filed: Aug. 11, 1986

[51] Int. Cl.⁵ .............................................. A61F 5/00
[52] U.S. Cl. ....................................................... 606/85
[58] Field of Search ........... 128/304, 305, 312, 92 VJ; 403/331, 324, 319; 606/85

[56] References Cited

U.S. PATENT DOCUMENTS

| D. 272,648 | 2/1984 | Bolesky et al. | D24/28 |
| D. 273,806 | 5/1984 | Bolesky et al. | D24/28 |
| D. 282,238 | 1/1986 | Kenna | D8/94 |
| D. 284,100 | 6/1986 | Kenna | D24/33 |
| 3,815,599 | 6/1974 | Deyerle | 128/305 |
| 3,874,003 | 4/1975 | Moser et al. | 128/92 C |
| 4,306,550 | 12/1981 | Forte | 128/92 E |
| 4,552,136 | 11/1985 | Kenna | 128/92 E |
| 4,583,270 | 4/1986 | Kenna | 29/80 |
| 4,587,964 | 5/1986 | Walker et al. | 128/92 E |
| 4,601,289 | 7/1986 | Chiarizzio et al. | 128/305 |

FOREIGN PATENT DOCUMENTS

| 0541949 | 6/1957 | Canada | 403/324 |
| 2032568 | 5/1980 | United Kingdom | 403/319 |

Primary Examiner—C. Fred Rosenbaum
Assistant Examiner—Denise W. DeFranco
Attorney, Agent, or Firm—Margaret L. Geringer

[57] ABSTRACT

A rasp tool comprises a handle and a cutter. The rasp tool carries a releasable locking assembly to couple the cutter to the handle. The releasable locking assembly is compactly arranged at the distal end of the handle and the mating proximal end of the cutter. The assembly includes a first interconnecting means for opposing longitudinal separation between the handle and the cutter, and a second interconnecting means for opposing lateral motion between the cutter and the handle. The releasable locking assembly provides an effective, simple to use, manually controllable means for attaching and detaching the cutter to the handle.

5 Claims, 2 Drawing Sheets

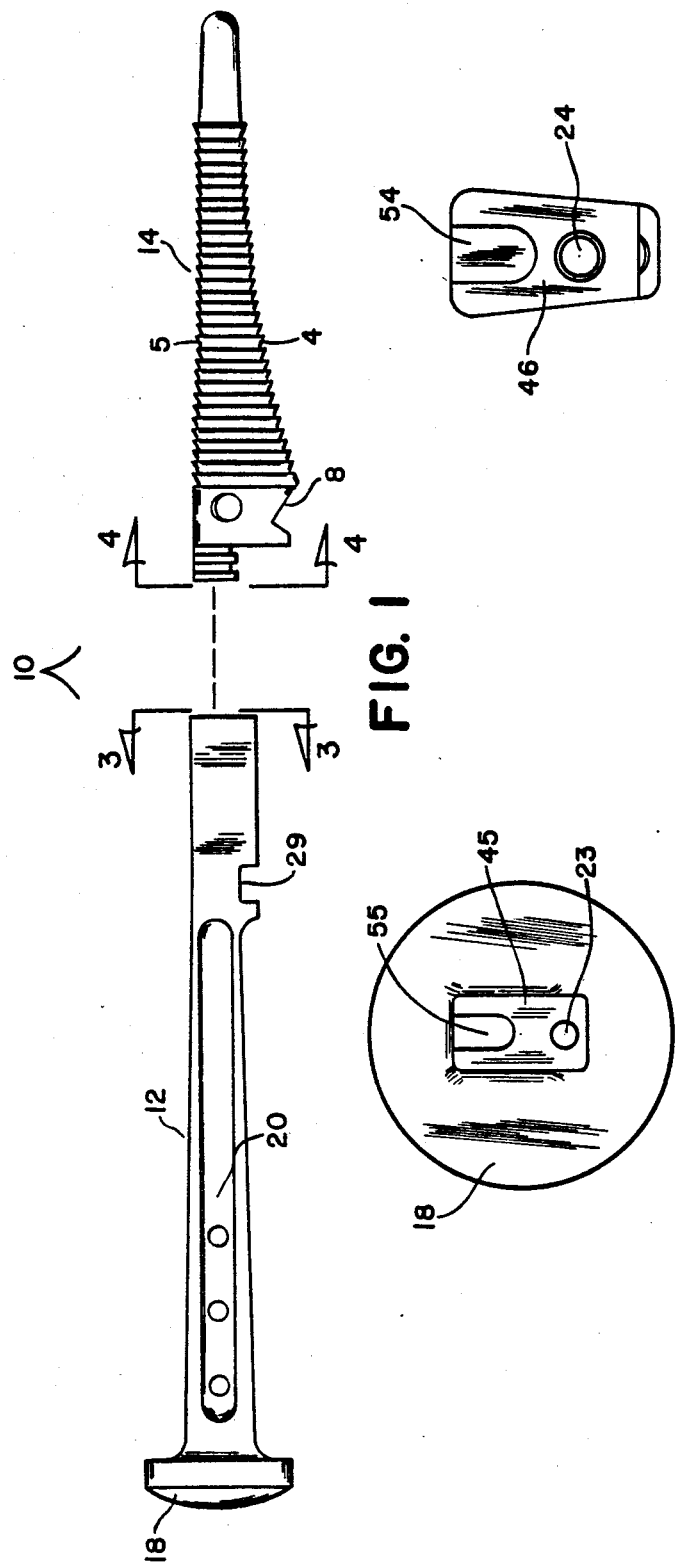
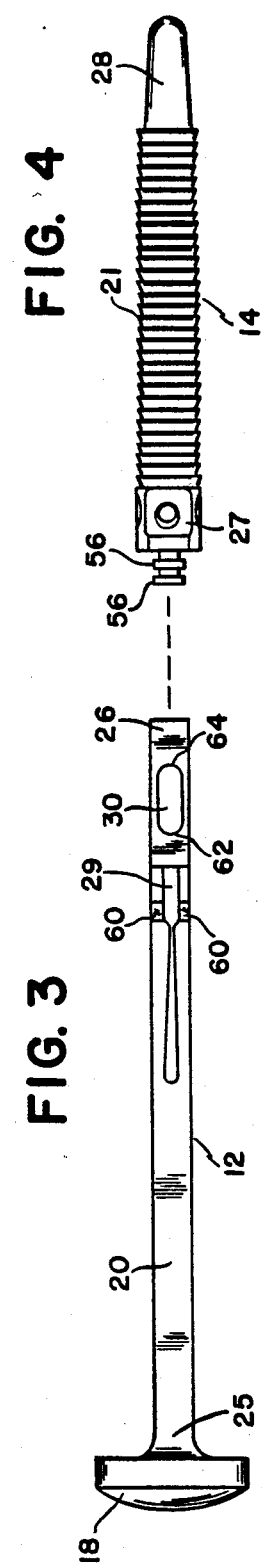

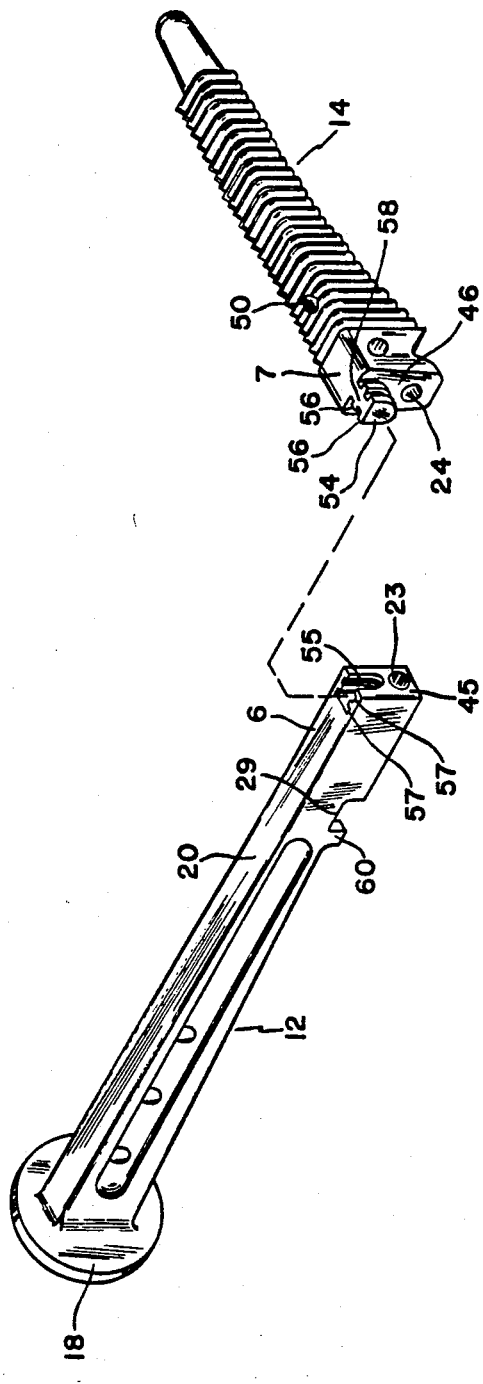
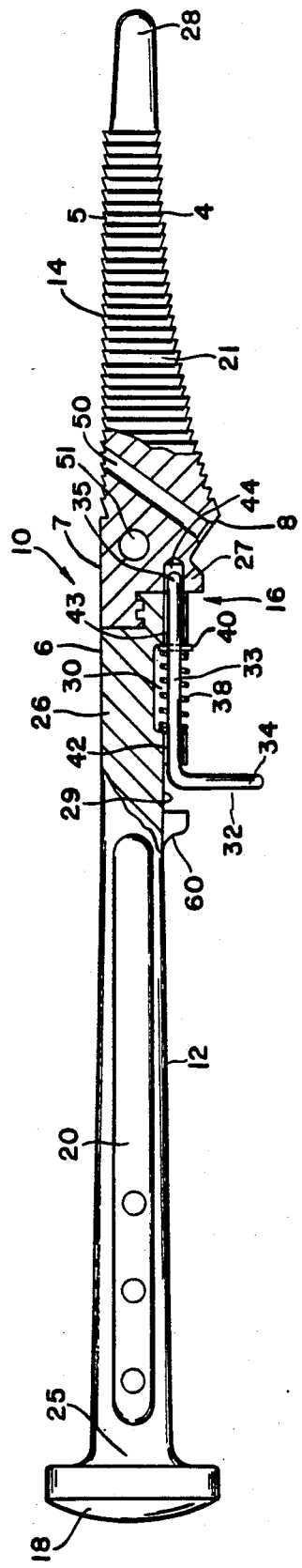

4,921,493

RASP TOOL

BACKGROUND OF THE INVENTION

The present invention relates to a rasp tool which is used by a surgeon to contour bone or the like. More specifically, the rasp tool is used where a femoral prosthesis is implanted in a femur.

It has been proposed to utilize a rasp tool with a handle that is releasable relative to a cutter, so that the handle can be removed after the initial rasping process of the femur. The cutter can remain lodged in the femur to enable further contouring of the proximal end of the femur, and also to enable the cutter to be used as a provisional or a trial implant by cooperating with mating head/neck provisional components in order to perform a trial joint reduction. Some such releasable handle and cutter assemblies are disclosed in the following U.S. Patents: U.S. Pat. No. 4,587,964 to Walker et al.; U.S. Pat. No. 4,583,270 to Kenna; U.S. Pat. No. 4,552,136 to Kenna; U.S. Pat. No. 4,306,550 to Forte; and U.S. Pat. No. 3,874,003 to Moser. Many of these tools are cumbersome and difficult to operate during surgery.

OBJECTS OF THE INVENTION

It is an object of the present invention to provide a simple and reliable releasable locking assembly which is conveniently located on a rasp tool to provide a secure, positive lock between the handle and the cutter.

SUMMARY OF THE INVENTION

The present invention teaches a simple, releasable locking assembly for a rasp tool providing a compact structure facilitating finger operation during surgery. Accordingly, the present invention covers a rasp tool for contouring bone or the like comprising a handle and a cutter, with a releasable locking assembly for selective interconnection of the handle and the cutter. The cutter is adapted to contour the bone. The releasable locking assembly includes a raised post extending from the proximal end of the cutter and a corresponding cut out portion extending into the distal end of the handle for fitting about the raised post. The post and cut out also provide a means for opposing longitudinal separation of the handle and cutter when the post is in cooperative engagement with the cut out. The releasable locking assembly further includes a longitudinally slideable locking pin in the handle which may selectively protrude from the distal end of the handle or be retracted into the handle. The proximal end of the cutter includes a blind bore aligned longitudinally with the locking pin to enable the locking pin to be selectively engaged in the blind bore such that when the locking pin is engaged in the bore, while the raised post is engaged in the corresponding cut out, the cutter will be securely attached to the handle. When the locking pin is engaged in the blind bore, this provides a means for opposing lateral motion between the handle and the cutter.

For the purposes of this invention, the term lateral motion is defined to mean movement in a direction generally toward the sides of the instrument. Longitudinal motion is defined to mean movement in a direction generally along the length of the instrument or toward or away from the distal end of the handle.

BRIEF DESCRIPTION OF THE DRAWINGS

In the drawings accompanying this application.

FIG. 1 is an exploded side view of the rasp tool of the present invention without the locking pin incorporated therein.

FIG. 2 is an exploded bottom side view of the rasp tool of FIG. 1.

FIG. 3 is an enlarged end view of the handle of the rasp tool taken along lines 3—3 of FIG. 1.

FIG. 4 is an enlarged end view of the cutter of the rasp tool taken along lines 4—4 of FIG. 1.

FIG. 5 is an exploded perspective view of the rasp tool of FIG. 1.

FIG. 6 is an assembled side view of the rasp tool of the present invention shown in partial cross-sectional.

DETAILED DESCRIPTION OF THE INVENTION

FIGS. 1-6 illustrate a particularly advantageous embodiment of a rasp tool according to the present invention.

The rasp tool 10 includes a handle 12 and a cutter 14 releasably coupled thereto by means of a releasable locking assembly 16. The handle 12 has a proximal end 25 and a distal end 26 with an elongated shaft 20 therebetween. The handle 12 is provided with an enlarged head 18 on the proximal end 25. The cutter 14 also includes a proximal end 27 and a distal end 28 with an intermediate cutting portion 21 therebetween.

Referring particularly to FIGS. 5-6, the releasable locking assembly 16 includes a raised post 54 extending from the proximal end 27 of the cutter 14 and a corresponding aperture or cut out portion 55 extending into the distal end 26 of the handle 12. The cut out or recess 55 is adapted to securely engage the post 54 by fitting thereabout. The internal shape of the cut out 55 conforms or mates with the external shape of the post 54. This assembly of the post 54 and cut out 55 provide a first cooperative interconnection means for opposing longitudinal separation of the cutter 14 and the handle 12. This first means conveniently utilizes a series of spaced, laterally protruding ribs 56 on the post 54, with a mating series of spaced grooves 57 in the cut out, although other suitable mechanisms could be utilized to oppose the longitudinal separation.

The proximal end 27 of the cutter 14 includes a substantially flat proximal face 46, while the distal end 26 of the handle 12 includes a substantially flat distal face 45. The widths of the ribs 56 and corresponding grooves 57 vary such that the cutter 14 and handle 12 can only be connected one way to ensure that the proximal cutter face 46 mates or contacts with the distal handle face 45 to provide maximum surface contact between the handle 12 and the cutter 14 when assembled.

It is further noted that the cut out 55 opens into the handle 12 from the distal handle face 45 and from one side of the handle 6. The raised post 54 is also located toward one side of the proximal face 46 in alignment with the cut out 55. One side 58 of the raised post 54 may be flush with the one side 7 of the cutter 14. Accordingly, side 58 of the post 54 is smooth, i.e. does not include the protruding ribs 56. Due to the cooperative engagement of the ribs 56 and grooves 57, the raised post 54 can only be inserted one way into the cut out 55. To engage the post 54 in the cut out 55, the raised post 54 is aligned with the cut out 55 and must slide laterally into the cut out 55 from the opening on the one side 6 of the handle 12. The locking pin 32 (to be discussed further below) must be retracted to assemble the post 54 into cut out 55. When assembled, this first interconnection means opposes longitudinal separation of the cutter 14 from the handle 12. In fact, this post 54/cut out 55 assembly also opposes lateral displacement or movement between the cutter 14 and the handle 12, except in the direction toward the cut out opening on the one side 6 of the handle 12. When assembled, the smooth side 58 of the post 54 is substantially flush with the one side 6 of the handle 12.

The releasable locking assembly 16 further includes a second cooperatively interconnecting means for opposing lateral movement between the cutter 14 and the handle 12, especially to oppose any lateral freedom of motion still available upon assembly of the first interconnection means. The second interconnection means includes a longitudinally slideable locking pin 32 in the handle 12, and corresponding blind bore 44 in the cutter 14 which is aligned longitudinally with the locking pin 32. The blind bore 44 opens out onto the proximal cutter face 46 at opening 24. The locking pin 32 may be selectively engaged with the blind bore 44 such that when the locking pin 32 is engaged in the bore 44, lateral motion between the cutter 14 and the handle 12 will be opposed in any lateral direction.

The locking pin 32 may be spring loaded with spring 38. The locking pin 32 has a rest position in which the distal tip 35 of the pin 32 protrudes from the distal handle face 45, and has a withdrawn position in which the distal tip 35 of the pin 32 is retracted into the handle 12.

The locking pin 32 may be conveniently "L-shaped" to form a trigger shaped pin, and has a first leg 33 and a second leg 34. The first leg 33 is aligned along the length of the handle 12, and the second leg 34 protrudes laterally from the handle 12 forming a manual actuating means. However, it is understood that other suitable configurations of the locking pin 32 may also be utilized.

The handle 12 includes a channel means including a first channel 42 and a second channel 43 in alignment therewith for retaining the first leg 33 of sliding pin 32. Channels 42 and 44 are in alignment with blind bore 44 so that when the distal tip 35 of locking pin 32 protrudes from the distal handle face 45, it will extend into blind bore 44 when the cutter 14 is attached to the handle 12. The distal tip 35 protrudes from the opening 23 of second channel 43 at the distal handle face 45. The first and second channels 42 and 43 are separated by an enlarged window 30 having a first end 62 and a second end 64. The window 30 provides an opening in a side of the handle 12 about the intermediate portion of the first leg 33 of the locking pin 32 for retaining the spring 38 about the first leg 33. The spring 38 surrounds the intermediate portion of the first leg 33 and is retained longitudinally between the first end 62 and second end 64 of window 30. The first leg 33 has a protruding pin 40 extending therethrough, located between the spring 38 and the second end 64 of the window 30, so that when the locking pin 32 is retracted toward the proximal end 25 of the handle 12 and into the withdrawn position, the protrusion 40 causes the spring to compress against the first end 62 of the window 30. Release of the locking pin 32 causes the spring 38 to return to its extended rest position, and thus causes the distal tip 35 of the locking pin 32 to protrude from the distal handle face 45.

The second leg 34 of trigger shaped pin 32 extends laterally from first channel 42 at trigger cut out 29. Alignment extensions 60 may also be provided.

In order to attach the cutter 14 to the handle 12, the second leg 34 of the pin 32 is manually pulled toward the proximal end 25 of the handle 12, retracting the distal tip 35 of the pin 32 into the handle 12. However, it is understood that other means of actuating or retracting pin 32 may be utilized. The raised, ribbed post 54 is then aligned with the corresponding grooved cut out 55. The post 54 is then slid laterally into the cut out 55 until fully seated, with the faces 45 and 46 in contact with each other. The second leg 34 of pin 32 is then released which causes the distal tip 35 of pin 32 to extend into blind bore 44, thus securely attaching the cutter 14 to the handle 12. The combined use of the first interconnecting means of the post 54/cut out 55 and the second interconnecting means of the locking pin 32/bore 44 opposes both longitudinal and lateral separation of the cutter 14 and handle 12, thereby providing a simple, but secure releasable locking assembly 16.

To release the handle 12 from the cutter 14, the pin 32 is again manually pulled toward the proximal end 25 of handle 12 to retract the pin 32 from engagement with the bore 44 of cutter 14. The handle 12 is then laterally slid away from the raised post 54 on the cutter 14, releasing the handle 12 from the cutter 14.

Channel 50, as shown in FIG. 6, may be provided on the cutter 14 to accept a mating extension (not shown) from other tools or provisional implant accessories that are to be used with the cutter 14 after the cutter 14 is in place in the bone and the handle 12 has been removed. Channel 50 extends from the angled surface 8 on the medial side 4 of the cutter 14 through the cutter 14, angling distally toward the lateral side 5. It is also noted that a hole 51 may be provided in the cutter 14 to aid in extraction of the cutter 14 from the bone.

It can readily be seen that the releasable locking assembly 16 of the present invention enables the handle 12 to be simply, quickly and effectively attached and detached to and from the cutter 14 with a minimum of moving parts. Since the spring loaded pin assembly 32 is the only moving part, there is less chance for the locking assembly 16 to fail. The pin 32 simply retracts and extends by selective manual sliding of the pin 32.

While this invention has been described and exemplified in terms of a particularly advantageous embodiment, those skilled in the art can appreciate that modifications can be made without departing from the spirit and scope of this invention.

We claim:
1. A rasp tool for contouring a bone or the like comprising a handle, a cutter and a releasable locking assembly for enabling selective interconnection of the handle and cutter, the cutter adapted to contour the bone, the handle including a proximal end and a distal end and the cutter including a proximal end and a distal end, the releasable locking assembly including a raised post extending from the proximal end of the cutter and a corresponding recess extending into the distal end of the handle for fitting about the raised post, the releasable locking assembly further including a slideable locking pin in the handle and the proximal end of the cutter including a blind bore aligned longitudinally with the locking pin to enable the locking pin to be selectively engaged in the blind bore such that when the locking pin is engaged in the bore while the raised post is captured in the corresponding recess, the cutter will be securely attached to the handle, the raised post and the corresponding recess being spaced apart from the slideable locking pin and blind bore such that the locking pin and blind bore are not directly contacting the raised post and recess.

2. The rasp tool of claim 1 wherein the proximal end of the cutter includes a substantially flat proximal face having a first side and a second side, and the distal end of the handle includes a mating substantially flat distal face having a first side and a second side, and wherein the handle has an outer elongated side extending from the first side of the distal face and wherein the raised post is located toward the first side of the proximal face in alignment with the corresponding recess which is located toward the first side of the distal face, the recess extending into the handle from the first side of the distal face and from the elongated side of the handle providing an opening to the recess from the first side of the distal face and an opening to the recess from the elongated side of the handle, and wherein the post and recess include a means for opposing longitudinal movement between the cutter and the handle, such that in order to engage the handle to the cutter, the raised post must laterally slide into the recess from the opening on the elongated side of the handle, the proximal face of the cutter being flush against the distal face of the handle while the locking pin is disengaged from the blind bore, then once the raised post is properly positioned in the corresponding recess, the slideable locking pin is released into engagement with the blind bore, opposing any further lateral sliding motion, thus securely locking the cutter and handle together.

3. The rasp tool of claim 2 wherein one side of the raised post is flush with one outer side of the cutter and when aligned and engaged with the recess in the handle, the one side of the raised post is also flush with the outer elongated side of the handle.

4. The rasp tool of claim 1 wherein the locking pin is spring loaded via a spring and has a rest position in which the pin protrudes from the distal face of the handle, and has a withdrawn position in which the pin is retracted into the handle.

5. A rasp tool for contouring a bone or the like comprising a handle, a cutter and a releasable locking assembly for enabling selective interconnection of the handle and cutter, the cutter adapted to contour the bone, the releasable locking assembly including first and second interconnecting means between the handle and the cutter, the first interconnecting means for opposing longitudinal separation between the handle and the cutter and the second interconnecting means for opposing lateral motion between the cutter and the handle, the first and second interconnecting means cooperating to secure the cutter to the handle wherein the handle has a distal surface and the cutter has a proximal surface, the distal and proximal surfaces forming a contact surface between the handle and the cutter, and wherein the first interconnecting means includes a fixed raised post extending from one of the faces and a recess in the other face for cooperating mating engagement with the post, the recess is open on one side to allow the post to slide laterally into the recess, the recess and post have a laterally protruding means cooperating therebetween to oppose longitudinal movement between the handle and the cutter, and wherein the second interconnecting means includes a selectively engageable pin member which is extendable and retractable from one of the faces and wherein the other face has a blind bore for accepting the extendable pin member, such that when the pin member is engaged in the bore, lateral movement between the handle and the cutter is opposed, thus the combined use of the first and second interconnecting means provides a secure attachment of the cutter to the handle when both are in engagement between the cutter and handle and wherein the first interconnecting means is distinct and spatially separated laterally apart from the second interconnecting means such that the first and second interconnecting means are not directly contacting each other and such that the extendable and retractable pin member is engageable with the blind bore but does not contact the fixed raised post.

* * * * *